United States Patent [19]

Curtis et al.

[11] Patent Number: 5,108,910
[45] Date of Patent: Apr. 28, 1992

[54] DNA SEQUENCES ENCODING FUSION PROTEINS COMPRISING GM-CSF AND IL-3

[75] Inventors: Benson M. Curtis; Linda S. Park, both of Seattle; David J. Cosman, Bainbridge Island, all of Wash.

[73] Assignee: Immunex Corporation, Seattle, Wash.

[21] Appl. No.: 674,288

[22] Filed: Mar. 22, 1991

Related U.S. Application Data

[60] Division of Ser. No. 567,983, Aug. 14, 1990, Pat. No. 5,073,627, which is a continuation-in-part of Ser. No. 397,146, Aug. 22, 1989, abandoned.

[51] Int. Cl.$^5$ .................... C12N 15/62; C12N 15/63; C07H 21/04
[52] U.S. Cl. .................. 435/69.7; 435/320.1; 435/172.3; 435/69.5; 435/69.52; 536/27
[58] Field of Search .............. 435/69.1, 69.7, 172.3, 435/320.1; 530/350, 351; 536/27

[56] References Cited

U.S. PATENT DOCUMENTS

| | | | |
|---|---|---|---|
| 4,935,233 | 6/1990 | Bell et al. | 424/85.5 |
| 5,032,395 | 7/1991 | Clark et al. | |

FOREIGN PATENT DOCUMENTS

| | | |
|---|---|---|
| 0276846 | 1/1988 | European Pat. Off. |
| 0282185 | 2/1988 | European Pat. Off. |
| 0288809 | 4/1988 | European Pat. Off. |
| 85/02863 | 12/1984 | World Int. Prop. O. |

OTHER PUBLICATIONS

Exp. Hematol. 15, 1007–1012, 1987, Williams et al. Interactions between Purified Murine Colony-Stimulating Factors on the in vitro proliferation of Purified Murine Granulocytes.

PNAS 88; 5809–5813, Jul. 1991, Curtis et al., Enhanced hematopoietic activity of a human granulocyte/macrophage colony stimulating factor–interleukin 3 fusion protein.

Donahue et al., *Human IL-3 and GM-CSF Act Synergistically in Stimulating Hematopoiesis in Primates,* Science 241:1820, 1988.

Broxmeyer et al., *Synergistic myelopoietic actions in vivo after administration to mice of combinations of purified natural murine colony-stimulating factor 1, recombinant murine interleukin 3, and recombinant murine granulocyte/macrophage colony-stimulating factor,* Proc. Natl. Acad. Sci. USA 84:3871, 1987.

Krumwieh et al., *Human Recombinant Derived IL-3 and GM-CSF in Hematopoiesis of Normal Cynomolgus Monkeys,* Behring Inst. Mitt. 83:250, 1988.

Park et al., *Heterogeneity in Human Interleukin-3 Receptors,* J. Biol. Chem. 264:5420, 1989.

Yang et al., *The Human Genes for GM-CSF and IL 3 are Closely Linked in Tandem on Chromosome 5,* Blood 71: 958, 1988.

Barlow et al., *Close genetic and physical linkage between the murine haemopoietic growth factor genes GM-CSF and Multi-CSF (IL3),* EMBO J. 6:617 1987.

Kelso et al., *Independent Regulation of Granulocyte–Macrophage Colony-Stimulating Factor and Multi-Lineage Colony-Stimulating Factor Production in T Lymphocyte Clones,* J. Immunol. 136:1718, 1986.

*Primary Examiner*—Garnette D. Draper
*Assistant Examiner*—John D. Ulm
*Attorney, Agent, or Firm*—Christopher L. Wight

[57] ABSTRACT

A DNA sequence encoding fusion protein is disclosed which comprises GM-CSF and IL-3. Such fusion proteins more biologically active than GM-CSF or IL-3 alone or GM-CSF and IL-3 combined.

15 Claims, 6 Drawing Sheets

Figure 1

| | | | | | | | | | | | | | | |
|---|---|---|---|---|---|---|---|---|---|---|---|---|---|---|
| GCT | CCA | GCT | AGA | TCT | CCA | TCT | CCA | TCT | ACT | CAA | CCA | TGG | GAA | CAC | 45 |
| Ala | Pro | Ala | Arg | Ser | Pro | Ser | Pro | Ser | Thr | Gln | Pro | Trp | Glu | His | 15 |
| GTT | AAC | CTC | ATT | CAA | GAA | GCT | TTG | CGT | CTC | CTG | GAC | CTG | AGT | AGA | 90 |
| Val | Asn | Ala | Ile | Gln | Glu | Ala | Leu | Arg | Leu | Leu | Asp | Leu | Ser | Arg | 30 |
| GAC | ACT | GCT | GCT | GAG | ATG | AAT | GAA | GAA | GTA | GAA | GTC | ATC | TCA | GAA | 135 |
| Asp | Thr | Ala | Ala | Glu | Met | Asn | Glu | Glu | Val | Glu | Val | Ile | Ser | Glu | 45 |
| ATG | TTT | GAC | CTC | CAG | GAG | CCG | ACC | TGC | CTA | CAG | ACC | CGC | CTG | GAG | 180 |
| Met | Phe | Asp | Leu | Gln | Glu | Pro | Thr | Cys | Leu | Gln | Thr | Arg | Leu | Glu | 60 |
| CTG | TAC | AAG | CAG | GGC | CTG | CGG | GGC | AGC | CTC | ACC | AAG | CTC | AAG | GGC | 225 |
| Leu | Tyr | Lys | Gln | Gly | Leu | Arg | Gly | Ser | Leu | Thr | Lys | Leu | Lys | Gly | 75 |
| CCC | TTG | ACC | ATG | ATG | GCC | AGC | CAC | TAC | AAA | CAG | CAC | TGC | CCT | CCA | 270 |
| Pro | Leu | Thr | Met | Met | Ala | Ser | His | Tyr | Lys | Gln | His | Cys | Pro | Pro | 90 |
| ACC | CCG | GAA | ACT | TCC | TGT | GCA | ACC | CAG | ATT | ATC | ACC | TTT | GAA | AGT | 315 |
| Thr | Pro | Glu | Thr | Ser | Cys | Ala | Thr | Gln | Ile | Ile | Thr | Phe | Glu | Ser | 105 |
| TTC | AAA | GAG | AAC | CTG | AAG | GAC | TTT | CTG | CTT | GTC | ATC | CCC | TTT | GAC | 360 |
| Phe | Lys | Glu | Asn | Leu | Lys | Asp | Phe | Leu | Leu | Val | Ile | Pro | Phe | Asp | 120 |
| TGC | TGG | GAG | CCA | GTC | CAG | GAG | ggt | ggc | ggt | gga | tcc | ggc | ggt | ggc | 405 |
| Cys | Trp | Glu | Pro | Val | Gln | Glu | Gly | Gly | Gly | Gly | Ser | Gly | Gly | Gly | 135 |
| ggc | ggc | tca | GCT | CCC | ATG | ACC | CAG | ACG | ACG | CCC | TTG | AAG | ACC | AGC | 450 |
| Gly | Gly | Ser | Ala | Pro | Met | Thr | Gln | Thr | Thr | Pro | Leu | Lys | Thr | Ser | 150 |
| TGG | GTT | GAT | TGC | TCT | AAC | ATG | ATC | GAT | GAA | ATT | ATA | ACA | CAC | TTA | 495 |
| Trp | Val | Asp | Cys | Ser | Asn | Met | Ile | Asp | Glu | Ile | Ile | Thr | His | Leu | 165 |
| AAG | CAG | CCA | CCT | TTG | CCT | TTG | CTG | GAC | TTC | AAC | AAC | CTC | AAT | GGG | 540 |
| Lys | Gln | Pro | Pro | Leu | Pro | Leu | Leu | Asp | Phe | Asn | Asn | Leu | Asn | Gly | 180 |
| GAA | GAC | CAA | GAC | ATT | CTG | ATG | GAA | AAT | AAC | CTT | CGA | AGG | CCA | AAC | 585 |
| Glu | Asp | Gln | Asp | Ile | Leu | Met | Glu | Asn | Asn | Leu | Arg | Arg | Pro | Asn | 195 |
| CTG | GAG | GCA | TTC | AAC | AGG | GCT | GTC | AAG | AGT | TTA | CAG | GAC | GCA | TCA | 630 |
| Leu | Glu | Ala | Phe | Asn | Arg | Ala | Val | Lys | Ser | Leu | Gln | Asp | Ala | Ser | 210 |
| GCA | ATT | GAG | AGC | ATT | CTT | AAA | AAT | CTC | CTG | CCA | TGT | CTG | CCC | CTG | 675 |
| Ala | Ile | Glu | Ser | Ile | Leu | Lys | Asn | Leu | Leu | Pro | Cys | Leu | Pro | Leu | 225 |
| GCC | ACG | GCC | GCA | CCC | ACG | CGA | CAT | CCA | ATC | CAT | ATC | AAG | GAC | GGT | 720 |
| Ala | Thr | Ala | Ala | Pro | Thr | Arg | His | Pro | Ile | His | Ile | Lys | Asp | Gly | 240 |
| GAC | TGG | AAT | GAA | TTC | CGG | AGG | AAA | CTG | ACG | TTC | TAT | CTG | AAA | ACC | 765 |
| Asp | Trp | Asn | Glu | Phe | Arg | Arg | Lys | Leu | Thr | Phe | Tyr | Leu | Lys | Thr | 255 |
| CTT | GAG | AAT | GCG | CAG | GCT | CAA | CAG | ACG | ACT | TTG | AGC | CTC | GCG | ATC | 810 |
| Leu | Glu | Asn | Ala | Gln | Ala | Gln | Gln | Thr | Thr | Leu | Ser | Leu | Ala | Ile | 270 |
| TTT | | | | | | | | | | | | | | | 813 |
| Phe | | | | | | | | | | | | | | | 271 |

Figure 2

```
GCT CCC ATG ACC CAG ACG ACG TCC TTG AAG ACC AGC TGG GTT GAT   45
Ala Pro Met Thr Gln Thr Thr Ser Leu Lys Thr Ser Trp Val Asp   15

TGC TCT AAC ATG ATC GAT GAA ATT ATA ACA CAC TTA AAG CAG CCA   90
Cys Ser Asn Met Ile Asp Glu Ile Ile Thr His Leu Lys Gln Pro   30

CCT TTG CCT TTG CTG GAC TTC AAC AAC CTC AAT GGG GAA GAC CAA   135
Pro Leu Pro Leu Leu Asp Phe Asn Asn Leu Asn Gly Glu Asp Gln   45

GAC ATT CTG ATG GAA AAT AAC CTT CGA AGG CCA AAC CTG GAG GCA   180
Asp Ile Leu Met Glu Asn Asn Leu Arg Arg Pro Asn Leu Glu Ala   60

TTC AAC AGG GCT GTC AAG AGT TTA CAG GAC GCA TCA GCA ATT GAG   225
Phe Asn Arg Ala Val Lys Ser Leu Gln Asp Ala Ser Ala Ile Glu   75

AGC ATT CTT AAA AAT CTC CTG CCA TGT CTG CCC CTG GCC ACG GCC   270
Ser Ile Leu Lys Asn Leu Leu Pro Cys Leu Pro Leu Ala Thr Ala   90

GCA CCC ACG CGA CAT CCA ATC CAT ATC AAG GAC GGT GAC TGG AAT   315
Ala Pro Thr Arg His Pro Ile His Ile Lys Asp Gly Asp Trp Asn   105

GAA TTC CGG AGG AAA CTG ACG TTC TAT CTG AAA ACC CTT GAG AAT   360
Glu Phe Arg Arg Lys Leu Thr Phe Tyr Leu Lys Thr Leu Glu Asn   120

GCG CAG GCT CAA CAG ACG ACT TTG AGC CTC GCG ATC TTT GGT GGC   405
Ala Gln Ala Gln Gln Thr Thr Leu Ser Leu Ala Ile Phe Gly Gly   135

GGT GGA TCC GGC GGT GGT GGA TCT GGT GGC GGC GGA TCT GCT CCA   450
Gly Gly Ser Gly Gly Gly Gly Ser Gly Gly Gly Gly Ser Ala Pro   150

GCT AGA TCT CCA TCT CCA TCT ACT CAA CCA TGG GAA CAC GTT AAC   495
Ala Arg Ser Pro Ser Pro Ser Thr Gln Pro Trp Glu His Val Asn   165

GTC ATT CAA GAA GCT TTG CGT CTC CTG GAC CTG AGT AGA GAC ACT   540
Ala Ile Gln Glu Ala Leu Arg Leu Leu Asp Leu Ser Arg Asp Thr   180

GCT GCT GAG ATG AAT GAA GAA GTA GAA GTC ATC TCA GAA ATG TTT   585
Ala Ala Glu Met Asn Glu Glu Val Glu Val Ile Ser Glu Met Phe   195

GAC CTC CAG GAG CCG ACC TGC CTA CAG ACC CGC CTG GAG CTG TAC   630
Asp Leu Gln Glu Pro Thr Cys Leu Gln Thr Arg Leu Glu Leu Tyr   210

AAG CAG GGC CTG CGG GGC AGC CTC ACC AAG CTC AAG GGC CCC TTG   675
Lys Gln Gly Leu Arg Gly Ser Leu Thr Lys Leu Lys Gly Pro Leu   225

ACC ATG ATG GCC AGC CAC TAC AAA CAG CAC TGC CCT CCA ACC CCG   720
Thr Met Met Ala Ser His Tyr Lys Gln His Cys Pro Pro Thr Pro   240

GAA ACT TCC TGT GCA ACC CAG ATT ATC ACC TTT GAA AGT TTC AAA   765
Glu Thr Ser Cys Ala Thr Gln Ile Ile Thr Phe Glu Ser Phe Lys   255

GAG AAC CTG AAG GAC TTT CTG CTT GTC ATC CCC TTT GAC TGC TGG   810
Glu Asn Leu Lys Asp Phe Leu Leu Val Ile Pro Phe Asp Cys Trp   270

GAG CCA GTC CAG GAG                                           825
Glu Pro Val Gln Glu                                           275
```

DNA SEQUENCES ENCODING FUSION PROTEINS COMPRISING GM-CSF AND IL-3

This application is a division of U.S. patent application Ser. No. 567,983, filed Aug. 14, 1990, now U.S. Pat. No. 5,073,627, which is a continuation in part of U.S. patent application Ser. No. 397,146, filed Aug. 22, 1989, now abandoned.

BACKGROUND OF THE INVENTION

The present invention relates generally to analogs of GM-CSF and IL-3 proteins, and particularly to the construction of fusion proteins comprising CM-CSF and IL-3.

The differentiation and proliferation of hematopoietic cells is regulated by secreted glycoproteins collectively known as colony-stimulating factors (CSFs). In humans, these proteins include granulocyte-macrophase CSF (GM-CSF), which promotes granulocyte and macrophage production from normal bone marrow, and which also appears to regulate the activity of mature, differentiated granulocytes and macrophages. IL-3 (also known as multi-CSF) also stimulates formation of a broad range of hematopoietic cells, including granulocytes, macrophages, eosinophils, mast cells, megakaryocytes and erythroid cells. GM-CSF and IL-3 thus have considerable overlap in their broad range of biological activities. Other CSFs have a more restricted range of activity, macrophage CSF (M-CSF) stimulating almost exclusively macrophage colony formation, and granulocyte CSF (G-CSF) stimulating primarily granulocyte colonies. Although GM-CSF and IL-3 have distinct amino acid sequences, preclinical studies indicate that they may be useful to treat various cytopenias, and to potentiate immune responsiveness to infectious pathogens, and to assist in reconstituting normal blood cell populations following viral infection or radiation or chemotherapy-induced hematopoietic cell suppression. The genes encoding GM-CSF and IL-3 are located on the same chromosome in mouse and man and the expression of the genes is linked in some cells, such as activated T lymphocytes (Kelso et al., *J. Immunol.* 136:1718, 1986; Yang et al., *Blood* 71:958, 1988; Barlow et al., *EMBO J.* 6:617, 1987).

Short-term experiments have demonstrated that the simultaneous combination of GM-CSF and IL-3 was more effective than either GM-CSF or IL-3 alone in increasing cycling rates and numbers of marrow hematopoietic progenitor cells in vitro in lactoferrin-treated mice (Broxmeyer et al., *Proc. Natl. Acad. Sci. USA* 84:3871, 1987). No such synergy has been observed in vivo for simultaneous administration of GM-CSF and IL-3, although clinical studies have shown that the consecutive administration of recombinant human IL-3 and recombinant human GM-CSF was more effective in raising white blood cell counts in normal cynomolgus monkeys than either GM-CSF or IL-3 along (Krumwieh et al., *Behring Inst. Mitt.* 83:250, 1988; Donahue et al., *Science* 241:1820, 1988).

The biological activities of GM-CSF and IL-3 are mediated by binding to specific cell surface receptors expressed on primary cells and in vitro cell lines. GM-CSF and IL-3 each bind to their respective receptor, resulting in transduction of a biological signal to various immune effector cells. Recent studies of the characteristics and distribution of the receptor for IL-3 on the human myelogenous leukemia cell line KG-1 and human pre-B cell line JM-1 indicate that a subclass of receptor exists which also binds GM-CSF (Park et al., *J. Biol. Chem.* 264:5420, 1989). These studies showed that human GM-CSF is capable of almost completely inhibiting the binding of $^{125}$I-IL-3 to KG-1 cells and, conversely, that IL-3 is capable of substantially inhibiting binding of $^{125}$I-GM-CSF to the same cells. This direct competition between GM-CSF and IL-3 for a single cell surface receptor indicates that a single receptor is capable of binding both GM-CSF and IL-3. Although is not yet clear whether the heterogeneity in IL-3 and GM-CSF binding is due to the existence of a receptor molecule which is distinct from that which binds IL-3 alone or GM-CSF alone, or whether IL-3 and GM-CSF receptors may exist as multisubunit complexes, composed of different ratios of IL-3 and GM-CSF binding proteins, the receptor(s) will be referred to herein as the GM-CSF/IL-3 receptor.

SUMMARY OF THE INVENTION

The present invention is a fusion protein comprising GM-CSF and IL-3. The fusion proteins have a formula selected from the group consisting of $$R_1—R_2, R_2—R_1, R_1—L—R_2 \text{ and } R_2—L—R_1$$

wherein $R_1$ is GM-CSF; $R_2$ is IL-3; and L is a linker peptide sequence. In preferred aspects of the present invention, GM-CSF and IL-3 are linked together via a linker sequence which does not interfere with the folding of either the GM-CSF or IL-3 domains.

The fusion proteins of the present invention are more biologically active than GM-CSF or IL-3 alone or in combination and, relative to IL-3, have a significantly higher affinity of binding to cell lines which have GM-CSF/IL-3 receptors compared to cell lines with only IL-3 or GM-CSF receptors.

BRIEF DESCRIPTION OF THE DRAWINGS

FIG. 1 is a nucleotide sequence and corresponding amino acid sequence of a human GM-CSF/IL-3 fusion protein. The fusion protein comprises GM-CSF (amino acids 1-127) and IL-3 (amino acids 139-271) linked via a linker sequence (amino acids 128-138).

FIG. 2 is a nucleotide sequence and corresponding amino acid sequence of a human IL-3/GM-CSF fusion protein. The fusion protein comprises IL-3 (amino acids 1-133) and GM-CSF (amino acids 149-275) linked via a linker sequence (amino acids 134-148).

DETAILED DESCRIPTION OF THE INVENTION

Definitions

Figure 3A:
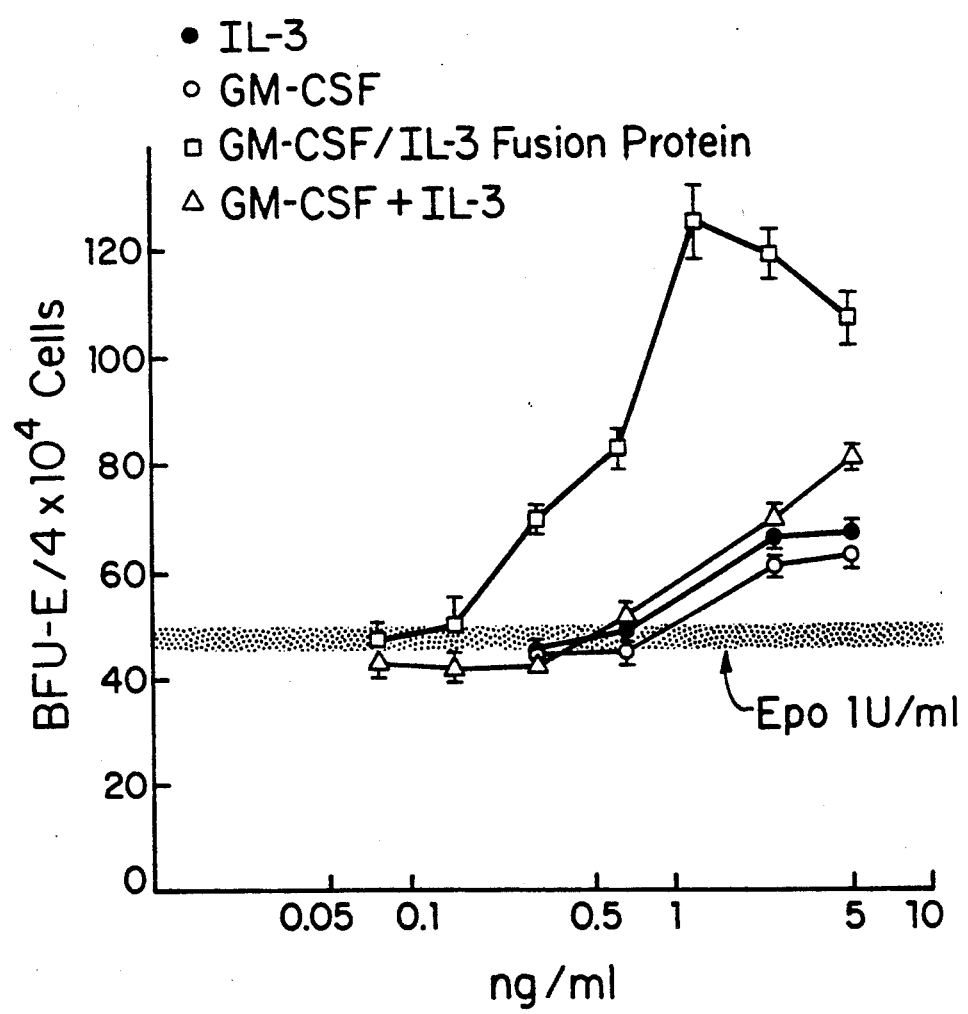
FIGS. 3A-3D are graphs showing that the GM-CSF/IL-3 fusion protein (□) enhances BFU-E (FIG. 3A), CFU-CM (FIGS. 3B and 3C) and CFU-GEMM (FIG. 3D) colony formation relative to IL-3 (●) or GM-CSF (O) alone, or to IL-3 and GM-CSF combined (Δ).
Figure 3B:
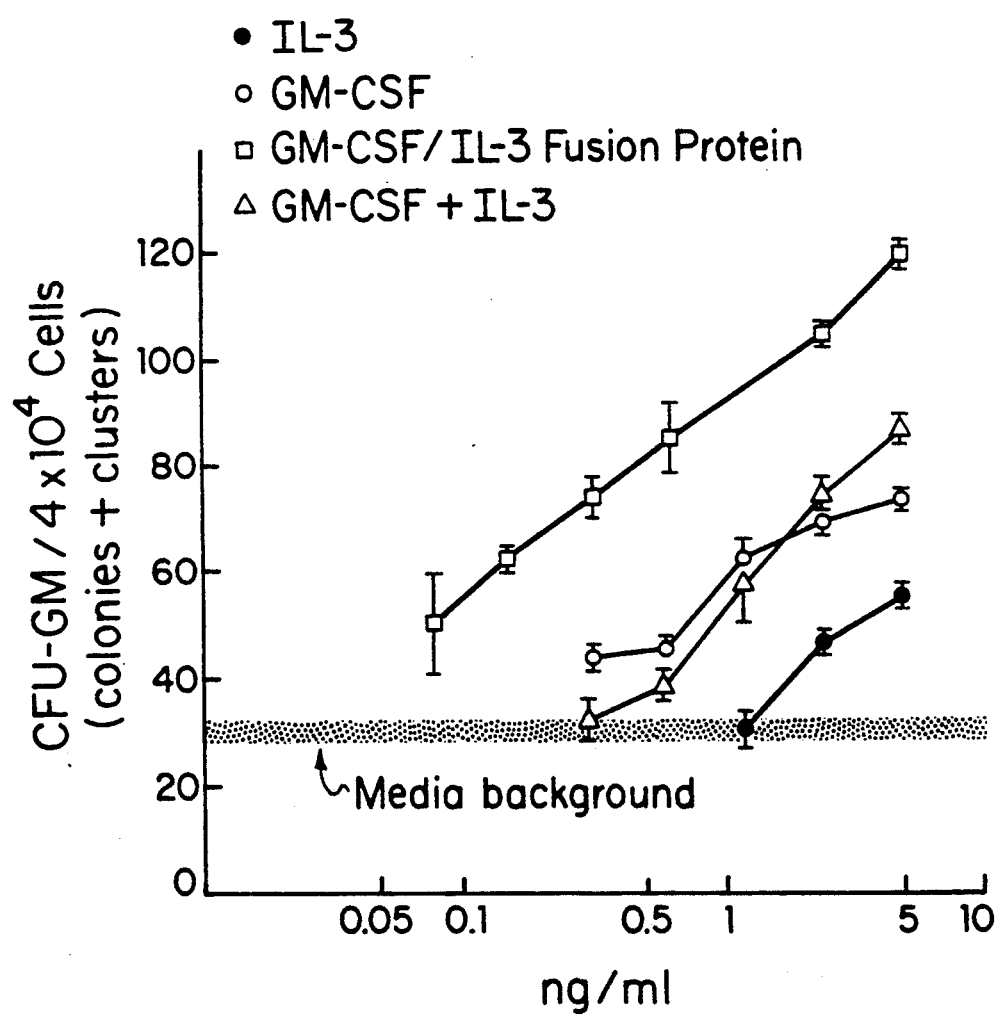
Figure 3C:
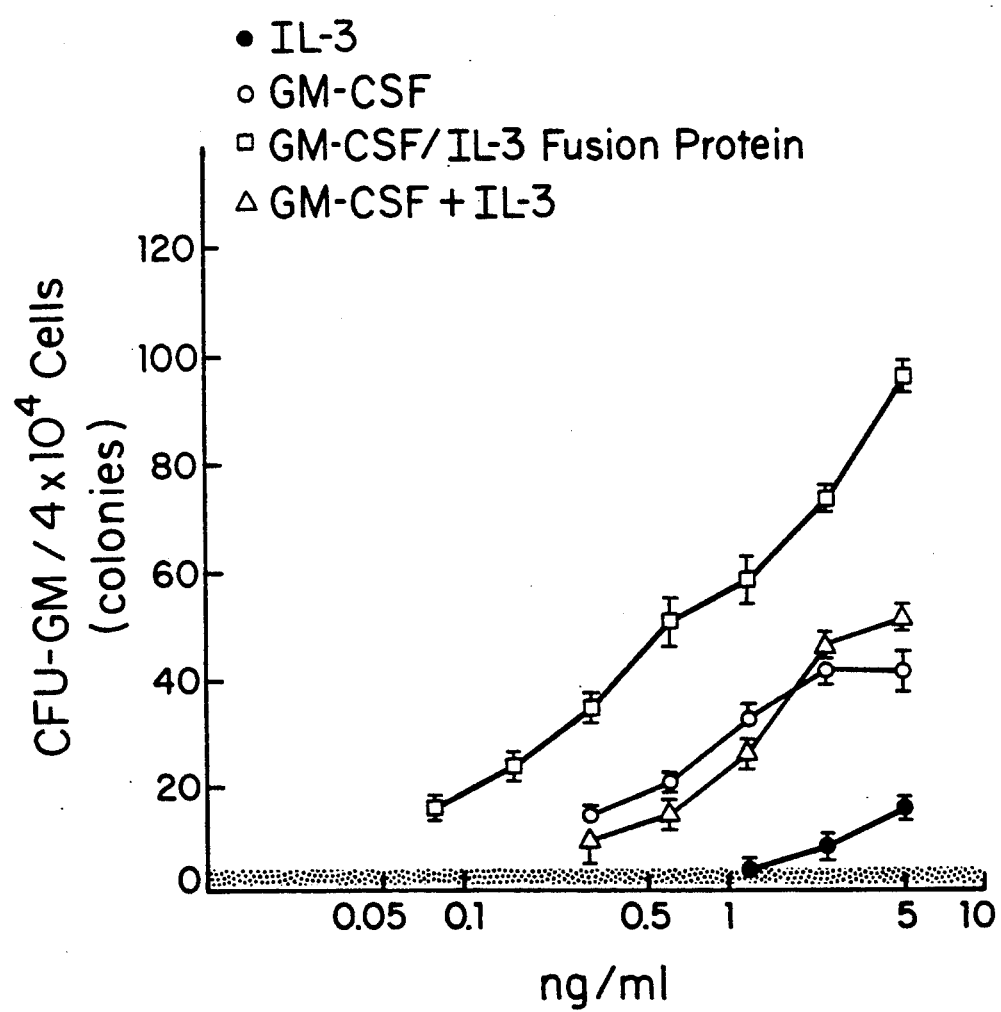
Figure 3D:
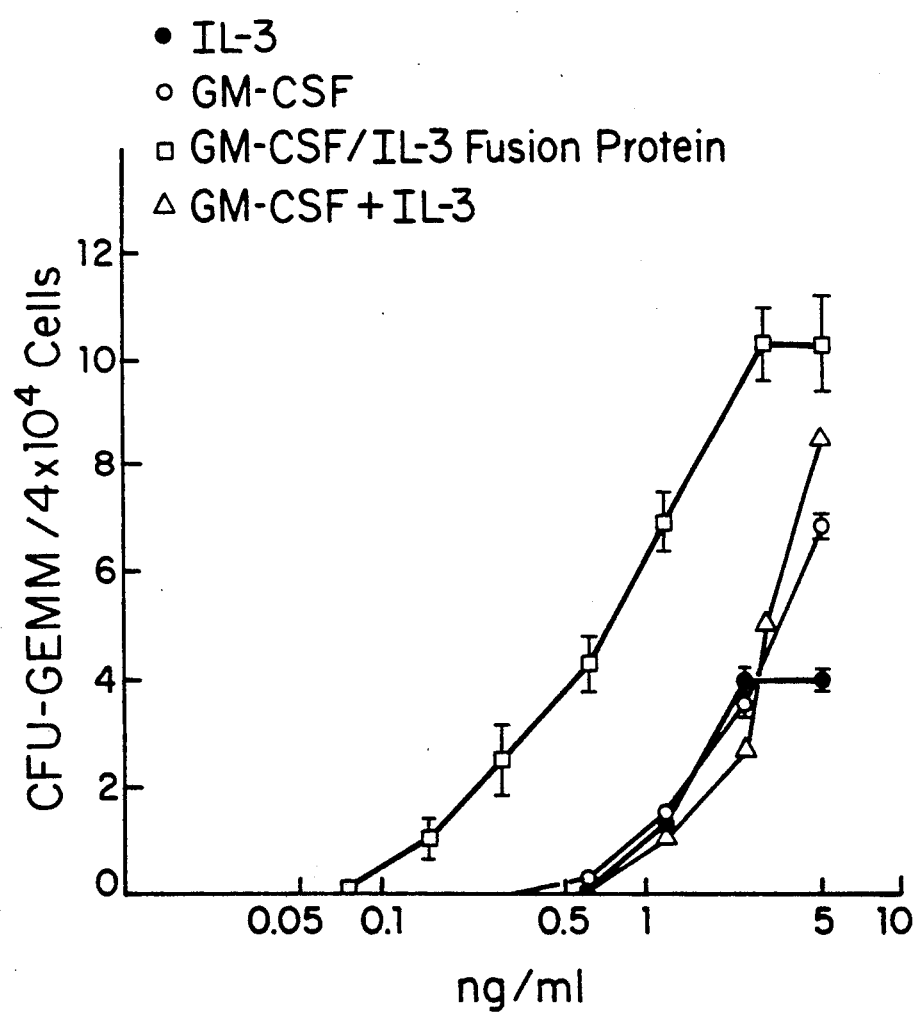

The term "GM-CSF" refers to proteins having amino acid sequences which are substantially similar to the native human granulocyte-macrophage colony-stimulating factor amino acid sequences (e.g., ATCC 53157) and which are biologically active in that they are capable of binding to GM-CSF receptors, transducing a biological signal initiated by binding GM-CSF receptors, or cross-reacting with anti-GM-CSF antibodies raised against GM-CSF. Such sequences are disclosed, for example, in Anderson et al., (*Proc. Nat'l Acad. Sci. USA* 82:6250, 1985). The term "GM-CSF" also includes analogs of GM-CSF molecules which exhibit at least some biological activity in common with native human GM-CSF. Exemplary analogs of GM-CSF are disclosed in EP Publ. No. 212914, which describes GM-CSF analogs having KEX2 protease cleavage sites inactivated so as to increase expression of GM-CSF in yeast hosts, and in WO Publ. No. 89/03881, which describes GM-CSF analogs having various glycosylation sites eliminated. Other GM-CSF analogs which are described herein may also be used to construct fusion proteins with IL-3. Furthermore, those skilled in the art of mutagenesis will appreciate that other analogs, as yet undisclosed or undiscovered, may be used to construct GM-CSF/IL-3 fusion proteins as described herein. A DNA sequence encoding a particularly preferred GM-CSF protein having potential glycosylation sites removes has been deposited with the American Type Culture Collection under accession number ATCC 67231 (GM-CSF[$Leu^{23}Asp^{27}Glu^{39}$]). The nomenclature used herein to specify amino acid sequences designates amino acids that differ from the native form in brackets immediately following the protein name and designated the species with which the protein is associated immediately preceding the protein name. Thus, huGM-CSF[$Leu^{23}Asp^{27}Glu^{29}$] refers to a human GM-CSF in which amino acid 23 has been changed to a leucine residue, amino acid 27 has been changed to an asparagine residue, and amino acid 29 has been changed to glutamic acid residue.

The term "IL-3" refers to proteins having amino acid sequences which are substantially similar to the native human Interleukin-3 amino acid sequences and which are biologically active in that they are capable of binding to IL-3 receptors or transducing a biological signal initiated by binding to IL-3 receptors, or cross-reacting with anti-IL-3 antibodies raised against IL-3. Such sequences are disclosed, for example, in EP Publ. Nos. 275,598 and 282,185. The term "IL-3" also includes analogs of IL-3 molecules which exhibit at least some biological activity in common with native IL-3. Examplary analogs of IL-3 are also disclosed in EP Publ. No. 282,185. Particularly preferred forms of IL-3 which may be fused to GM-CSF in accordance with the present invention include huIL-3[$Pro^8Asp^{15}Asp^{70}$], huIL-3[$Ser^8Asp^{15}Asp^{70}$], and huIL-3[$Ser^8$]. A DNA sequence encoding another IL-3 protein suitable for incorporation into fusion proteins as described herein is on deposit with ATCC under accession number ATCC 67747.

As used herein, the term "fusion protein" refers to a C-terminal to N-terminal fusion of GM-CSF and IL-3. The fusion proteins of the present invention include constructs in which the C-terminal portion of GM-CSF is fused to the N-terminal portion of IL-3, and also constructs in which the C-terminal portion of IL-3 is fused to the N-terminal portion of GM-CSF. Specifically, the fusion proteins of the present invention have a formula selected from the group consisting of

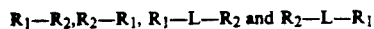

$R_1-R_2, R_2-R_1, R_1-L-R_2$ and $R_2-L-R_1$ wherein $R_1$ is GM-CSF; $R_2$ is IL-3; and L is a linker peptide sequence. GM-CSF is linked to IL-3 in such a manner as to produce a single protein which retains the biological activity of GM-CSF and IL-3. Specific fusion protein constructs are named by listing the GM-CSF and IL-3 domains in the fusion protein in their order of occurrence (with the N terminal domain specified first, followed by the C-terminal domain). Thus, GM-CSF/IL-3 refers to a fusion protein comprising GM-CSF followed by IL-3 (i.e., the C-terminus of GM-CSF is linked to the N-terminus of IL-3). Unless otherwise specified, the terms GM-CSF/IL-3 and IL-3/GM-CSF refer to fusion proteins with a linker sequence added. Similarly, huGM-CSF [$Leu^{23}As^{27}Glu^{39}$]/huIL-3[$Pro^8Asp^{70}$] refers to a fusion protein in which the N-terminal region of the fusion construct is huGM-CSF[$Leu^{23}As^{27}Glu^{39}$], and the C-terminal region is huIL-3[$Pro^8Asp^{15}Asp^{70}$].

The term "substantially identical," when used to define either amino acid or nucleic acid sequences, means that a particular subject sequence, for example, a mutant sequence, is substantially full-length and varies from the sequence of FIGS. 1 or 2 by one or more substitutions, deletions, or additions, the net effect of which is to retain biological activity of the protein when derived as a GM-CSF/IL-3 or IL-3/GM-CSF fusion protein. Alternatively, DNA analog sequences are "substantially identical" to the specific DNA sequences disclosed herein if: (a) the DNA analog sequence is derived from substantially the entire coding regions of the native mammalian GM-CSF and IL-3 genes; or (b) the DNA analog sequence is comparable in length with and capable of hybridization to DNA sequences of (a) under moderately stringent conditions and which encode biologically active GM-CSF or IL-3 molecules; or (c) DNA sequences which are degenerate as a result of the genetic code to the DNA analog sequences defined in (a) or (b) and which encode biologically active GM-CSF or IL-3 molecules. Substantially identical analog proteins will be greater than about 80 percent similar to the corresponding sequence of the native protein. Sequences having lesser degrees of similarly but comparable biological activity are considered to be equivalents. In defining nucleic acid sequences, all subject nucleic acid sequences capable of encoding substantially similar amino acid sequences are considered substantially similar to a reference nucleic acid sequence.

Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math.* 2:482,1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., E. coli, will be free of glycan. Protein expressed in yeast may have a glycosylation pattern different from that expressed in mammalian cells.

"Biologically active," as used throughout the specification means that a particular molecule shares sufficient amino acid sequence similarity with the embodiments of the present invention disclosed herein to be capable of binding to GM-CSF receptor, IL-3 receptor or GM-CSF/IL-3 receptor (see, e.g., Park et al., J. Biol. Chem. 264:5420, 1989), transmitting a GM-CSF and/or IL-3 stimulus to a cell, or cross-reacting with antibodies raised against GM-CSF or IL-3.

"DNA sequence" refers to a DNA polymer, in the form of a separate fragment or as a component of a larger DNA construct. Preferably, the DNA sequences are in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided of this invention can be assembled from cDNA fragments and short oligonucleotide linkers, or from a series of oligonucleotides, to provide a synthetic gene which is capable of being expressed in a recombinant transcriptional unit.

"Recombinant expression vector" refers to a replicable DNA construct used either to amplify or to express DNA which encodes the fusion proteins of the present invention and which includes a transcriptional unit comprising an assembly of (1) a genetic element or elements having a regulatory role in gene expression, for example, promoters or enhancers, (2) a structure or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally by subsequently cleaved from the expressed recombinant protein to provide a final product. "Recombinant microbial expression system" means a substantially homogeneous monoculture of suitable host microorganisms, for example, bacteria such as E. coli or yeast such as S. cerevisiae, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Construction of cDNA Sequences Encoding Fusion Proteins Comprising GM-CSF and IL-3

A DNA sequence encoding a fusion protein is constructed using recombinant DNA techniques to assemble separate DNA a fragments encoding GM-CSF and IL-3 into an appropriate expression vector. The 3' end of a DNA fragment encoding GM-CSF is ligated to the 5' end of the DNA fragment encoding IL-3, with the reading frames of the sequences in phase to permit mRNA translation of the sequences into a single biologically active fusion protein. The resulting protein is huGM-CSF[Leu$^{23}$Asp$^{27}$Glu$^{39}$]/huIL-3[Pro$^{8}$Asp$^{15}$Asp$^{70}$]. Alternatively, the 3' end of a DNA fragment encoding IL-3 may be ligated to the 5' end of the DNA fragment encoding GM-CSF, with the reading frames of the sequences in phase to permit mRNA translation of the sequences into a single biologically active fusion protein, yielding the protein huIL-3[Pro$^{8}$Asp$^{15}$Asp$^{70}$]-/huGM-CSF[Leu$^{23}$Asp$^{27}$Glu$^{39}$]. The regulatory elements responsible for transcription of DNA into mRNA are retained on the first of the two DNA sequences, while binding signals or stop codons, which would prevent read-through to the second DNA sequence, are eliminated. Conversely, regulatory elements are removed from the second DNA sequence while stop codons required to end translation are retained.

In preferred aspects of the present invention, means are provided for linking the GM-CSF and IL-3 domains, preferably via a linker sequence. The linker sequence separates GM-CSF and IL-3 domains by a distance sufficient to ensure that each domain properly folds into its secondary and tertiary structures. Suitable linker sequences (1) will adopt a flexible extended conformation, (2) will not exhibit a propensity for developing an ordered secondary structure which could interact with the functional GM-CSF and IL-3 domains, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, may also be used in the linker sequence.

The length of the linker sequence may vary without significantly affecting the biological activity of the fusion protein. For example, the GM-CSF and IL-3 proteins may be directly fused without a linker sequence. Linker sequences are unnecessary where the proteins being fused have non-essential N- or C-terminal amino acid regions which can be used to separate the functional domains and prevent steric interference. In one preferred embodiment of the present invention, the C-terminus of GM-CSF may be directly fused to the N-terminus of IL-3. GM-CSF has six amino acids following the C-terminal cysteine residue, which is involved in disulfide bonding and is essential for proper folding of the protein. IL-3 has 15 amino acids preceding its N-terminal cysteine residue. The combined terminal regions thus may provide sufficient separation to render the use of a linker sequence unnecessary.

Generally, the two protein domains will be separated by distance approximately equal to the small unit dimension of GM-CSF or IL-3 (i.e., approximately 0.38 nm, as determined by analogy with similar four-helix hormones). In a preferred aspect of the invention, a linker sequence length of about 11 amino acids is used to provide a suitable separation of functional protein domains, although longer linker sequences may also be used. The length of the linker sequence separating GM-CSF and IL-3 is from 1 to 500 amino acids in length, or more preferably from 1 to 100 amino acids in length. In the most preferred aspects of the present invention, the linker sequence is from about 1–20 amino acids in length. In the specific embodiments disclosed herein, the linker sequence is from about 5 to about 15 amino acids, and is advantageously from about 10 to about 15 amino acids. Amino acids sequences useful as linkers of GM-CSF and IL-3 include, by way of example, (Gly$_4$Ser)$_3$ and Gly$_4$SerGly$_5$Ser.

The linker sequence is incorporated into the fusion protein construct by well known standard methods of mutagenesis as described below.

Proteins and Analogs

The present invention provides a fusion protein comprising a human GM-CSF and human IL-3. Derivatives of the fusion proteins of the present invention also include various structural forms of the primary protein which retain biological activity. Due to the presence of ionizable amino and carboxyl groups, for example, a fusion protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini. Other derivatives of the fusion protein within the scope of this invention include covalent or aggregative conjugates of the fusion protein with other proteins or polypeptides, such as by synthesis in recombinant culture as N- or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast a-factor leader). Peptides may also be added to facilitate purification or identification of GM-CSF/IL-3 fusion proteins (e.g., poly-His). The amino acid sequence of the fusion protein can also be linked to the peptide Asp-Tyr-Lys-Asp-Asp-Asp-Asp-Lys(-DYKDDDDK) (Hopp et al., *Bio/Technology* 6:1204, 1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli.*

Fusion protein derivatives may also be used as immunogens, reagents in receptor-based immunoassays, or as binding agents for affinity purification procedures of binding ligands. Derivatives may also be obtained by cross-linking agents, such as M-maleimidobenzoyl succinimide ester and N-hydroxysuccinimide, at cysteine and lysine residues. Fusion proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking).

The present invention also includes proteins with or without associated native-pattern glycosylation. Expression of DNAs encoding the fusion proteins in bacteria such as *E. coli* provides non-glycosylated molecules. Functional mutant analogs having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-A$_1$-Z, where A$_1$ is any amino acid except Pro, and Z is Ser or Thr. In this sequence, asparagine provides a side chain amino groups for covalent attachment of carbohydrate. Such a site can be eliminated by substituting another amino acid for Asn or for residue Z, deleting Asn or Z, or inserting a non-Z amino acid between A$_1$ and Z, or an amino acid other than Asn between Asn and A$_1$. Examples of human GM-CSF analogs in which glycosylation sites have been removed include huGM-CSF[Leu$^{23}$Asp$^{27}$Glu$^{39}$], huGM-CSF[Leu$^{23}$], huGM-CSF[Leu$^{23}$Asp$^{27}$], huGM-CSF[Glu$^{39}$], huGM-CSF[Asp$^{27}$Glu$^{39}$], huGM-CSF[Leu$^{23}$Glu$^{39}$] and huGM-CSF[Asp$^{27}$]. Examples of human IL-3 analogs in which glycosylation sites have been removed include huIL-3[Pro$^8$Asp$^{15}$Asp $^{70}$], huIL-3[Asp$^{70}$], huIL-3[Asp$^{15}$Asp$^{70}$], huIL-3[Pro$^8$Asp$^{15}$], huIL-3[Pro$^8$Asp$^{70}$], and huIL-3[Asp$^{15}$].

Derivatives and analogs may also be obtained by mutations of the fusion protein. A derivative or analog, as referred to herein, is a polypeptide in which the GM-CSF and IL-3 domains are substantially homologous to full-length GM-CSF and IL-3 domains of the sequences disclosed in FIGS. 1 and 2 but which has an amino acid sequence difference attributable to a deletion, insertion or substitution.

Bioequivalent analogs of fusion proteins may be constructed by, for example, making various substitutions of residues or sequences. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physiochemical characteristics resembling those of the reside to be replaced. Similarly, when a deletion or insertion strategy is adopted, the potential effect of the deletion or insertion on biological activity should be considered.

Mutations in nucleotide sequences constructed for expression of analogs must, of course, preserve the reading frame phase of the coding sequences and preferably will not create complementary regions that could hybridize to produce secondary mRNA structures such as loops or hairpins which would adversely affect translation of the GM-CSF/IL-3 receptor mRNA. Although a mutation site may be predetermined, it is not necessary that the nature of the mutation per se be predetermined.

For example, in order to select for optimum characteristics of mutants at a given site, random mutagenesis may be conducted at the target codon and the expressed mutants screened for the desired activity.

Not all mutations in nucleotide sequences which encode fusion proteins comprising GM-CSF and IL-3 will be expressed in the final product, for example, nucleotide substitutions may be made to enhance expression, primarily to avoid secondary structure loops in the transcribed mRNA (see EPA 75,444A, incorporated herein by reference), or to provide codons that are more easily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981); and U.S. Pat. Nos. 4,518,584 and 4,737,462, and are incorporated by reference herein.

Expression of Recombinant Fusion Proteins Comprising GM-CSF and IL-3

The present invention provides recombinant expression vectors which include synthetic or cDNA-derived DNA fragments encoding human fusion proteins comprising GM-CSF and IL-3 or bioequivalent analogs operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

Due to code degeneracy, there can be considerable variation in nucleotide sequences encoding the same amino acid sequence; exemplary DNA embodiments are those corresponding to the nucleotide sequences shown in FIGS. 1 or 2. Other embodiments include sequences commensurate in length with and capable of hybridizing to the sequences of FIGS. 1 or 2 under moderately stringent conditions (50° C., 2 X SSC) and which encode biologically active fusion proteins.

Transformed host cells are cells which have been transformed or transfected with fusion protein vectors constructed using recombinant DNA techniques. Transformed host cells ordinarily express the desired fusion protein, but host cells transformed for purposes of cloning or amplifying DNA do not need to express the protein. Expressed fusion protein will generally be secreted into the culture supernatant. Suitable host cells for expression of fusion protein include prokaryotes, yeast or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed to produce fusion protein using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual,* Elsevier, New York, 1985), the relevant disclosure of which is hereby incorporated by reference.

Prokaryotic expression hosts may be used for expression of fusion protein that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium,* and various species within the genera Pseudomonas, Strepomyces, and Staphyolococcus, although other may also be employed as a matter of choice.

Useful expression vectors for bacterial use can comprise a selectable marker and bacterial origin of replication derived form commercially available plasmids comprising genetic elements of the well-known cloning vector pBR322 (ATCC 37017). Such commerical vectors include, for example, pKK223-3 (Pharmacia Fine Chemicals, Uppsala, Sweden) and pGEM1 (Promega Biotec, Madison, Wis., U.S.A.). These pBR322 "backbone" sections are combined with an appropriate promoter and the structural sequence to be expressed. *E coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the b-lactamase (penicillinase) and lactose promoter system (Change et. al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual,* Cold Spring Harbor Laboratory, p. 412, 1982). A particularly useful bacterial expression system employs the phage λ $P_L$ promoter and cI857ts thermoinducible repressor. Plasmid vectors available from the American Type Culture Collection which incorporate derivatives of the λ $P_L$ promoter include plasmid pHUB2, resident in *E. coli* strain JMB9 (ATCC 37092) and pPlc28, resident in *E. coli* RR1 (ATCC 53082).

Recombinant fusion proteins may also be expressed in yeast hosts, preferably from the Saccharomyces species, such as *S. cerevisiae*. Yeast of other genera such as Pichia or Kluyveromyces may also be employed. Yeast vectors will generally contain an origin of replication from the 2m yeast plasmid or an autonomously replicating sequence (ARS), promoter, DNA encoding the fusion protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeats lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glocose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. U.S.A.* 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. U.S.A.* 75:1929, 1978, selecting for Trp+ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% of yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived form the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily form the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

Particularly preferred eukaryotic vectors for expression of GM-CSF/IL-3 DNA include pIXY321 and pIXY344, both of which are yeast expression vectors derived from pBC102.K22 (ATCC 67,255) and contain DNA sequences from pBR322 for selection and replication in *E. coli* (Apr gene and origin of replication) and yeast, as described below in Examples 1 and 7.

Purified mammalian fusion proteins or analogs are prepared by culturing suitable host/vector systems to express the recombinant translation products of the DNAs of the present invention, which are then purified form culture media or cell extracts.

For example, supernatants from systems which secrete recombinant protein into culture media can be first concentrated using a commercially available protein concentration filter, for example, an Amicon or Millipore ultrafiltration unit. Following the concentration step, the concentrate can be applied to a suitable purification matrix. For example, a suitable affinity matrix can comprise a GM-CSF or IL-3 receptor or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a fusion protein composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can be disrupted by any convenient method, including freez-thaw cycling, sonication, mechanical disruption, or use of cell lysing agents.

Fermentation of yeast which express fusion proteins as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant murine GM-CSF on a preparative HPLC column.

Fusion protein synthesized in recombinant culture is characterized by the presence of non-human cell components, including proteins, in amounts and of a character which depend upon the purification steps taken to recover the fusion protein from the culture. These components ordinarily will be of yeast, prokaryotic or non-human higher eukaryotic origin and preferably are present in innocuous contaminant quantities, on the order of less than about 5 percent by scanning densitometry or chromatography. Further, recombinant cell culture enables the production of the fusion protein free of proteins which may be normally associated with GM-CSF or IL-3 as they are found in nature in their respective species of origin, e.g., in cells, cell exudates or body fluids.

Fusion protein compositions are prepared for administration by mixing fusion protein having the desired degree of purity with physiologically acceptable carriers. Such carriers will be nontoxic to recipients at the dosages and concentrations employed. Ordinarily, the preparation of such compositions entails combining the fusion protein with buffers, antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients.

Fusion protein compositions may be used to enhance proliferation, differentiation and functional activation of hematopoietic progenitor cells, such as bone marrow cells. Specifically, compositions containing the fusion protein may be used to increase peripheral blood leukocyte numbers and increase circulating granulocyte counts in myelosuppressed patients. To achieve this result, a therapeutically effective quantity of a fusion protein composition is administered to a mammal, preferably a human, in association with a pharmaceutical carrier or diluent.

The following examples are offered by way of illustration, and not by way of limitation.

EXAMPLES

Example 1

Synthesis of cDNAs Encoding GM-CSF/IL-3 Fusion Protein

A. Isolation of cDNA encoding huIL-3

Peripheral blood lymphocytes were isolated from buffy coats prepared from whole blood (Portland Red Cross, Portland, Oreg. USA) by Ficoll hypaque density centrifugation. T cells were isolated by rosetting with 2-aminoethylthiouronium bromide-treated sheep red blood cells. Cells were cultrued in 175 cm$^2$ flasks at $5 \times 10^6$ cells/ml for 18 hour in 100 ml RPMI, 10% fetal calf serum, 50 µM b-mercaptoethanol, 1% phytohemagglutinin (PHA) and 10 ng/ml phorbol 12-myristate 13-acetate (PMA). RNA was extracted by the guanidinium CsCl method and poly A+ RNA prepared by oligo-dT cellulose chromatography (Maniatis et al., *Molecular Cloning: A Laboratory Manual*, Cold Spring Harbor, 1982). cDNA was prepared from poly A+ RNA essentially as described by Gubler and Hoffman, *Gene* 25:263–269 (1983). The cDNA was rendered double-stranded using DNA polymerase I, blunt-ended with T4 DNA polymerase, methylated with EcoR1 methylase to protect EcoR1 cleavage sites within the cDNA, and ligated to EcoR1 linkers. These constructs were digested with EcoR1 to remove all but one copy of the linkers at each end of the cDNA, ligated to EcoR1-cut and dephosphorylated arms of phage λgt10 (Huynh et al., *DNA Cloning: A practical Approach*, Glover, ed., IRL Press, pp, 49–78) and packaged into λ phage extracts (Stratagene, San Diego, Calif., USA) according to the manufacturer's instructions. 500,000 recombinants were plated on *E. coli* strain C600hfl- and screened by standard plaque hybridization techniques using the following probes.

Two oligonucleotides were synthesized, with sequences complementary to selected 5' and 3' sequences of the huIL-3 gene. The 5' probe, complementary to a sequence encoding part of the huIL-3 leader, had the sequence 5'-GAGTTGGAGCAGGAGCAGGAC-3'. The 3' probe, corresponding to a region encoding amino acids 123–130 of the mature protein, had the sequence 5'-GATCGCGAGGCTCAAAGTCGT-3'. The method of synthesis was a standard automated triester method substantially similar to that disclosed by Sood et al., *Nucl. Acids Res.* 4:2557 (1977) and Hirose et al., *Tet. Lett.* 28:2449 (1978). Following synthesis, oligonucleotides were deblocked and purified by preparative gel electrophoresis. For use as screening probes, the oligonucleotides were terminally radiolabeled with 32P-ATP and T4 polynucleotide kinase using techniques similar to those disclosed by Maniatis et al. The *E. coli* strain used for library screening was C600hfl- (Huynh et al., 1985, supra).

Thirteen positive plaques were purified and reprobed separately with the two hybridization probes. Eleven clones hybridized to both oligonucleotides. The cDNA inserts from several positive recombinant phage were subcloned into an EcoR1-cut derivative (pGEMBL18) of the standard cloning vector pBR322 containing a polylinker having a unique EcoR1 site, a BamH1 site and numerous other unique restriction sites. An exemplary vector of this type, pGEMBL, is described by Dente et al., *Nucl. Acids Res.* 11:1645 (1983), in which the promoters for SP6 and T7 polymerases flank the multiple cloning sites. The nucleotide sequences of selected clones were determined by the chain termination method. Specifically, partial EcoR1 digestion of λGT10:IL-3 clones 2, 3, 4 and 5 yielded fragments ranging from 850 bp to 1,000 bp in size which were separately subcloned into the EcoR1 site of pGEMBL18. The inserts of the pGEMBL:rhuIL-3 subclones were sequenced using a universal primer that binds adjacent to the multiple cloning site of pGEMBL18, and synthetic oligonucleotide primers derived from the huIL-3 sequence.

B. Modification of N-Glycosylation Sites Encoded by huIL-3 cDNA and Assembly of Expression Vector for rhuIL-3 (Pro$^8$Asp$^{15}$Asp$^{70}$).

The two asparagine-linked glycosylation sites present in the natural protein (Asn$^{15}$ and Asn$^{70}$) were altered by changing the codons at these positions to ones that encode aspartic acid. This prevents N-linked glycosylation (often hyperglycosylation) of the secreted protein by the yeast cells, and a more homogeneous product is obtained. These changes were made as described below upon subcloning the huIL-3 cDNA into the yeast expression vector pIXY120.

The yeast expression vector pIXY120 is substantially identical to pBC102-K22, described in EPA 243,153, except that the following synthetic oligonucleotide containing multiple cloning sites was inserted from the Asp718 site (amino acid 79) near the 3' end of the a-factor signal peptide to the Spe1 site contained in the 2μ sequences:

fusion to the rhuIL-3 protein allows detection with antibody specific for the octapeptide and was used initially for monitoring the expression and purification of rhuIL-3. This oligonucleotide also encodes an amino acid change at position 15 (Asn$^{15}$ to Asp$^{15}$) to alter this N-linked glycosylation site. The underlined nucleotides in oligonucleotide A represent changes from the wild type cDNA sequence. Only the A to G and C to T changes at nucleotides 43 and 45, repectively (counting from the codon corresponding to the N-terminal alanine of the mature huIL-3 molecule), result in an amino acid change (Asp$^{15}$). The other base changes introduce convenient restriction sites (AhaII and PvuII) without altering the amino acid sequence. The resulting plasmid was designated pIXY139 and contains a rhuIL-3 cDNA with one remaining N-linked glycosylation consensus sequence (Asn$^{70}$).

Plasmid pIXY139 was used to perform oligonucleotide-directed mutagenesis to remove the second N-linked glycosylation consensus sequence by changing Asn$^{70}$ to Asp$^{70}$. The in vitro mutagensis was conducted by a method similar to that described by Walder and Walder, Gene 42:133 (1986). The yeast vector, pIXY139, contains the origin of replication for the single-stranded bacteriophage f1 and is capable of generating single-stranded DNA when present in a suitable (male) strain of E. coli and superinfected with helper phage.

Single-stranded DNA was generated by transforming E. coli strain JM107 and superinfecting with helper phage IR1. Single-stranded DNA was isolated and annealed to the following mutagenic oligonucleotide B,

```
Asp718                                                                      /NcoI
GTACCTTTGGATAAAAGAGACTACAAGGACGACGATGACAAGAGGCCTCCATGGATCCCCCGGGACA
    GAAACCTATTTTCTCTGATGTTCCTGCTGCTACTGTTCTCCGGAGGTACCTAGGGGGCCCTGTGATC
                                                              /BamH1        SpeI
```

In addition, a 514-bp DNA fragment derived from the single-stranded bacteriophage f1 containing the origin of replication and intergenic region was inserted at the Nru1 site in the pBR322 DNA sequences. The presence of the f1 origin of replicaiton enables generation of single-stranded copies of the vector when transformed into appropriate (male) strains of E. coli and superinfected with bacteriophage f1. This capability facilitates DNA sequencing of the vector and allows the possibility of in vitro mutagenesis.

The yeast expression vector pIXY120 was digested with the restriction enzymes Asp718, which cleaves near the 3' end of the α-factor leader peptide (nucleotide 237), and BamH1, which cleaves in the polylinker. The large vector fragment was purified and ligated to the following DNA fragments: (1) a huIL-3 cDNA fragment derived from plasmid GEMBL18:huIL0-3 from the ClaI site (nucleotide 58 of mature huIL-3) to the BamH1site (3' to the huIL-3 cDNA in a polylinker); and (2) the following synthetic oligonucleotide linker A:

GTC AAG AGT TTA CAG GAC GCA TCA GCA AAT G, which provides a codon switch substituting Asp for Asn at position 70 of mature huIL-3. Annealing and yeast transformation conditions were done as described by Walder and Walder, supra. Yeast transformants were selected by growth on medium lacking tryptophan, pooled, and DNA extracted as described by Holm et al., Gene 42:169 (1986). This DNA, containing a mixture of wild type and mutant plasmid DNA, was used to transform E. coli RR1 to ampicillin resistance. The resulting colonies were screened by hybridization to radiolabeled oligonucleotide B using standard techniques. Plasmids comprising DNA encoding huIL-3 Asp$^{70}$ were identified by the hybridization to radiolabeled oligonucleotide B under stringent conditions and verified by nucleotide sequencing.

The resulting yeast expression plasmid was designated pIXY138, and contained the huIL-3 gene encoding the Asp$^{15}$ Asp$^{70}$ amino acid changes and the octapeptide DYKDDDDK at the N-terminus. The final yeast expression plasmid is identical to pIXY138 except

```
GTA CCT TTG GAT AAA AGA GAC TAC AAG GAC GAC GAT GAC AAG GCT CCC ATG ACC CAG
    GA AAC CTA TTT TCT GTG ATG TTC CTG CTG CTA CTG TTC CGA GGG TAC TGG GTC

ACG ACG CCC TTG AAG ACC AGC TGG GTT GAT TGC TCT AAC ATG AT
TGC TGC GGG AAC TTC TGG TCG ACC CAA CTA ACG AGA TTG TAC TAG C
```

Oligonucleotide A regenerates the sequence encoding the C-terminus of the α-factor leader peptide and fusing it in-frame to the octapeptide DYKDDDDK, which is, in turn, fused to the N-terminus of mature rhuIL-3. This that it lacks the nucleotide sequences coding for the octapeptide, thus generating mature rhuIL-3 as the product.

The final yeast expression plasmid was constructed as described below. The yeast expression vector pIXY120 was cleaved with the restriction enzymes Asp718 and methods similar to those described by Walder and Walder, supra. The following oligonucleotide was then synthesized

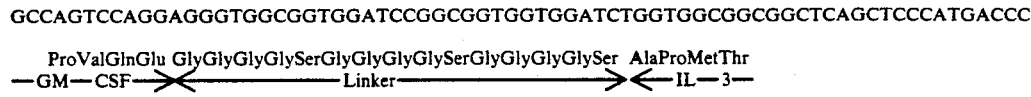

```
GCCAGTCCAGGAGGGTGGCGGTGGATCCGGCGGTGGTGGATCTGGTGGCGGCGGCTCAGCTCCCATGACCC
```

ProValGlnGlu GlyGlyGlyGlySerGlyGlyGlyGlySerGlyGlyGlyGlySer AlaProMetThr
—GM—CSF—>< ————————Linker———————————>< —IL—3—

BamH1 as described above. The large vector fragment was ligated together with (1) a huIL-3 cDNA fragment derived from plasmid pIXY138 that extended from the Aha2 site (which cleaves a nucleotide 19 of mature huIL-3) to the BamH1 site 3' to the cDNA, and (2) the following synthetic oligonucleotide C:

```
GTA CCT TTG GAT AAA AGA GCT CCC ATG ACC CAG ACG A
    GA AAC CTA TTT TCT CGT GGG TAC TGG GTC TGC TGC
    Pro Leu Asp Lys Arg Ala Pro Met Thr Gln Thr Thr
```

Oligonucleotide C regenerates the 3' end of the α-factor leader peptide from the Asp718 site (the amino acids Pro-Leu-Asp-lys-Arg) and the N-terminal seven amino acids of huIL-3 to the AhaII site. The resulting plasmid was designated pIXY151. This vector, when present in yeast, allows glucose-regulated expression and secretion of rhuIL-3 (Pro[8] Asp[15] Asp[70]).

C. Expression Vector for rhuGM-CSF (Leu[23], Asp[27], Glu[39]) Containing Modified N-Glycosylation Sites The wild-type gene coding for human GM-CSF, resident on plasmid pHG23, has been deposited with the American Type Culture Collection (ATCC), 12301 Parklawn Drive, Rockville, Md. 20852, USA, under accession number 39900. The wild-type gene inserted in a yeast expression vector, pYαfHuGM, has also been deposited with the ATCC under accession number 53157. In order to provide a non-glycosylated analog of human GM-CSF, oligonucleotide-directed site-specific mutagenesis procedures were employed to eliminate potential N-glycosylation sites, as described in PCT publication WO 89/03881. A plasmid encoding this analog, huGM-CSF (Leu[23] Asp[27] Glu[39]), was deposited with the ATCC as plasmid L207-3 in *E. coli* strain RR1 under accession number 67231.

Example 2

D. Construction of Expression Vector for GM-CSF/IL-3 Fusion Protein

In order to create a secretion vector for expressing a fusion construct having human GM-CSF and human IL-3 separated by a linker sequence, a precursor plasmid was first constructed by directly fusing DNAs encoding GM-CSF and IL-3 together without regard to reading frame or intervening sequences. A cDNA fragment encoding nonglycosylated human GM-CSF was excised from plasmid L207-3 as a 977bp restriction fragment (Sph1 to Ssp1). The IL-3 cDNA was excised from pIXY151 by digestion with Asp718, which was then blunt ended using the T4 polymerase reaction of Maniatas et al. (*Molecular Cloning: A Laboratory Manual,* Cold Spring Harbor, 1982, p. 118) and further digested with XhoI giving an 803 bp fragment. These two fragments were then directly ligated to a pIXY151 vector fragment cut with Sph1 and XhoI. This plasmid was called GM/IL-3 direct fusion.

The GM/IL-3 direct fusion plasmid was used as a template in oligonucleotide-directed mutagenesis using methods similar to those described by Walder and Walder, supra. The following oligonucleotide was then synthesized This oligonucleotide overlaps the 3' end of GM-CSF by 13 bp but does not include the stop codon, contains the Gly Ser linker, and overlaps the 5' end of IL-3 by 13 bp. The linker sequence was a modified version of the linker described by Huston et al. (*Proc. Natl. Acad. Sci. USA* 85:5879–5883, 1988) but was optimized for codon usage in yeast as per Bennetzen et al. (*J. Biol. Chem.* 257:3026, 1982).

Single stranded plasmid DNA was made from the GM/IL-3 direct fusion using R408 helper phage (Stratagene) and the methods of Russel et al. (*Gene* 45:333–338, 1986). Oligonucleotide directed mutagenesis was then carried out by annealing the above oligonucleotide to the single stranded plasmid DNA and transforming yeast strain XV2181 with annealed DNA as described by Walder and Walder, supra. The yeast vector contains the origin of replication for the single stranded bacteriophage f1 and is capable of sponsoring single stranded DNA production when present in a suitable (male) strain of *E. coli* and superinfected with helper phage. Yeast transformants were selected by growth on medium lacking tryptophan, pooled, and DNA was extracted as described by Holm et al. (*Gene* 42:169, 1986). This DNA, containing a mixture of mutant and wild type plasmid DNA, was used to transform *E. coli* RR1 to ampicillin resistance. The resulting colonies were screened by hybridization to radiolabeled oligonucleotide using standard techniques. Plasmids comprising DNA encoding GM-CSF/linker/IL-3 were identified by their hybridization to radiolabeled oligonucleotide containing the linker under stringent conditions and verified by nucleotide sequencing.

During nucleotide sequencing it was discovered that a mutation had occurred within the linker region. The nucleotide sequence TGGTGGATCTGG was deleted (see sequence), resulting in the expression of a protein in which the sequence of amino acids GlyGlySerGly were deleted. This mutation did not change the reading frame or prevent expression of a biologically active protein. The resulting plasmid was designated pIXY321 and expressed the fusion protein huGM-CSF[Leu[23]Asp[27]Glu[39]]/Gly4SerGly5Ser/huIL-3[Pro[8]Asp[15]Asp[70]].

EXAMPLE 3

Expression and Purification of GM-CSF/IL-3 Fusion Protein

The host strain, XV2181, a diploid *S. cerevisiae* strain, was formed by mating XV617-1-3 B [a, his6, leu2-1, trpl-1, ura 3, ste5], obtained from the University of Washington, Department of Genetics Yeast Strain Bank, Seattle, WASH., USA, and X2181-1B [a, trpl-1, gal1, ade1, his2], obtained from the Yeast Genetic Stock Center, University of California, Berkeley, CALIF., USA. The host strain was transformed with the expression plasmid by the method of Sherman et al., *Laboratory Course Manual for Methods in Yeast Genetics*, Cold Spring Harbor Laboratory, 1986.

Yeast containing the expression plasmid pIXY321 (see 1D, above) was maintained on YNB-trp agar plates stored at 4° C. A preculture was started by inoculating several isolated recombinant yeast colonies into one liter of YNB-trp medium (6.7 g/L Yeast Nitrogen Base, 5 g/L casamino acids, 40 mg/L adenine, 160 mg/L uracil, and 200 mg/L tyrosine), and was grown overnight in two 2-liter flasks at 30° C. with vigorous shaking. By morning the culture was saturated, in stationary phase, at an $OD_{600}$ of 2 to 7. The fermenters (three machines of 10 liter working volume), previously cleaned and sterilized, were filled to 80% of their working capacity with SD-2 medium (4.0 g/L ammonium sulfate, 3.2 g/L monobasic potassium phosphate, 3.0 g/L yeast extract, 1.0 g/L citric acid, 0.1 g/L sodium chloride, 5 ml/L 2% calcium chloride, 2.5 ml/L vitamin 101 solution, 0.5 ml/L trace elements solution, 0.5 ml/L 20% magnesium sulfate, 2.0 ml/L glucose) and maintained at 30° C. with 500–600 rpm agitation and 10–16 lpm aeration. The inoculum was added. After two hours of growth a nutrient feed of 50% glucose was begun at a rate such that 50 g/L is added over a period of 10–12 hours. The nutrient feed was then shifted to 50% ethanol added at 30–40 ml/hr until harvest.

Total elapsed time of fermentation was approximately 20 hours, after which optical density (600 nm) ranged from 30 to 45. The fermenters were then cooled to 20° C., pH of the yeast beer was adjusted to 8.0 by the addition of 5M NaOH, and the resulting material filtered through a Millipore Pellicon filler system equipped with a 0.45 μm filter cassette, and collected in a sterile 10 L carboy.

One liter of yeast supernatant containing GM-CSF/IL-3 fusion protein was concentrated to 50 ml on an Amicon YM-10 membrane. The yeast broth concentrate was then further purified by preparative HPLC by applying to a 1 cm×25 cm column packed with 5μ C-18 silica (Vydac, Separations Group, Hesperia, CALIF., USA) that was equilibrated in 0.1% trifluoroacetic acid in water (Solvent A) prior to application of the yeast concentrate. Alternatively, the crude yeast broth can be pumped directly on to the C-18 column. Following application of the material, the column was flushed with Solvent A until the optical absorbance of the effluent approached base line values. At this time a gradient of 0.1% trifluoroacetic acid in acetonitrile (Solvent B) was established from 0% B to 100% B at a rate of change of 1–2% B per minute and at a flow rate of 2 ml/minute. One minute fractions were collected. Aliquots of the fractions were analyzed for protein content by dot blot with a rabbit polyclonal antisera to IL-3. GM-CSF/IL-3 eluted in fraction 50 at approximately 50% acetonitrile.

HPLC fractions which were positive for GM-CSF/IL-3 fusion protein by dot blot were pooled and bound to SP-Sepharose in 20 mM β-alanine, pH 4. Fusion protein was eluted with 0.5M NaCl, 100 mM Tris-HCl, pH 8. Fractions containing fusion protein were identified by SDS-PAGE.

The ion exchange fractions containing protein having a molecular weight of 35,000 were pooled, concentrated to 100 μl and further purified by FPLC gel filtration on a Superose 12 column. The column was eluted with PBS. Fractions containing only the purified 35,000 MW fusion protein were identified by SDS-PAGE.

The biological activities (units/mg) and binding affinities of the GM-CSF/IL-3 prepared substantially as described above were determined as set forth in Examples 4 and 5.

EXAMPLE 4

Biological Activity of GM-CSF/IL-3 Fusion Protein in Thymidine Incorporation Assay In order to determine its level of biological activity, the GM-CSF/IL-3 fusion protein prepared as described in Example 3 was assayed for ability to stimulate proliferation of AML-193 cells in a thymidine incorporation assay. The AML-193 cell line is a GM-CSF dependent human monocytic leukemia cell line originally described by Santoli et al. (*J. Immunol.* 139:3348, 1987). The cells were grown in Iscove's Modified Dulbecco's Media (IMDM) with 25 mM HEPES, 200 nM L-glutamine, 5 μg/ml insulin 5 μg/ml transferrin, 5 ng/ml sodium selenite, 2.5% heat inactivated fetal bovine serum, antibiotics, and 5 ng/ml of purified recombinant human GM-CSF. The cells were split twice weekly and were seeded into fresh medium at a density of 300,000/ml.

A thymidine incorporation assay was employed to examine the capacity of known growth factors and unknown supernatants to stimulate proliferation of AML-193. AML-193 cells were washed by centrifugation and resuspended in assay medium composed of IMDM as above except that fetal calf serum and/or GM-CSF was not included. Pure GM-CSF, IL-3 or GM-CSF/IL-3 fusion protein was added to the first well of a 96 well flat bottom tissue culture plate at a final concentration of 400 ng/ml in 50 ml of medium. These samples were then serially diluted by 3-fold through the additional 11 wells of the microtitre plate. Fifty μl of medium containing 3750 AML-193 cells was added to each well and plates were incubated at 37° C. for 138 hours in a fully humidified atmosphere of 6% $CO_2$ in air. Tritiated thymidine (0.5 mCi/well) was added to each well for an additional 6 hours of incubation and the samples were harvested with an automated sample harvester and counted by liquid scintillation. One unit of activity is defined as the amount of growth factor required to stimulate half-maximal thymidine incorporation.

Simultaneous titration of IL-3, GM-CSF or GM-CSF/IL-3 fusion protein at identical concentrations revealed that the fusion protein was a more potent proliferation stimulus than either factor alone or IL-3 and GM-CSF combined. The specific activity of the IL-3, GM-CSF and GM-CSF/IL-3 fusion protein is set forth in Table A, below.

TABLE A

| Molecule | Specific Activity |
|---|---|
| IL-3 | $1.65 \times 10^5$ |
| GM-CSF | $9.74 \times 10^4$ |
| IL-3 + GM-CSF | $1.39 \times 10^5$ |
| GM-CSF/IL-3 | $1.81 \times 10^6$ |

The specific activity of GM-CSF/IL-3 fusion protein is approximately 10-fold higher than IL-3 or GM-CSF alone or GM-CSF plus IL-3 combined.

EXAMPLE 5

Binding Activity of GM-CS/IL-3 Fusion Protein in Equilibrium Binding Assay

Binding affinities of human IL-3, GM-CSF and fusion protein for receptors on human cells lines were determined by inhibition of $^{125}$I-labeled IL-3 or GM-CSF binding.

A. Radiolabeling of GM-CSF and IL-3. Recombinant human GM-CSF/IL-3 fusion protein was expressed in yeast cells and purified substantially as described above. Recombinant human IL-3 and GM-CSF, engineered to contain the octapeptide DYKDDDDK was expressed in yeast and purified using a monoclonal antibody specific to the octapeptide substantially as described in Hopp et al. (*Bio/Technology* 6:1204, 1988). The purified GM-CSF and IL-3 proteins were radiolabeled using a commercially available enzymobead radioiodination reagent (BioRad), substantially as described by Park et al. (*J. Biol. Chem.* 261:4177, 1986). Briefly, 2-10 μg of recombinant protein in 50 μl 0.2M sodium phosphate, pH 7.2, was combined with 50 μl enzymobead reagent, 2 mCi of sodium iodide in 20 μl of 0.05M sodium phosphate pH 7 and 10 μl of 2.5% β-D-glucose. After 10 min at 25° C., sodium azide (10 μl of 50 mM) and sodium metabisulfite (10 μl of 5 mg/ml) were added sequentially and incubation continued for 5 minutes at 25° C. The reaction mixture was fractionated by gel filtration on a 2 ml bed volume of Sephadex G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes, pH 7.4 (binding medium). The final pools of $^{125}$I-IL-3 and $^{125}$I-GM-CSF were diluted to a working stock solution of $1 \times 10^{-7}$M in binding medium and stored for up to one month at 4° C. without detectable loss of receptor binding activity. The specific activity of radiolabeled preparation of GM-CSF is routinely in the range of $1-5 \times 10^{15}$ cpm/mmole. The specific activity of IL-3 is in the range of $3-6 \times 10^{15}$ cpm/mmole.

B. Binding Assays. Binding assays were performed using JM-1, KG-1, HL-60 and AML-193 cells. JM-1, HL-60 and KG-1 cells were obtained and prepared as described by Park et al. (*J. Biol. Chem.* 264:5420, 1989). AML-193 cells were obtained and prepared as described above in Example 4. As described by Park et al. (supra), $^{125}$I-GM-CSF does not bind to JM-1 cells nor does GM-CSF inhibit binding of $^{125}$I-IL-3 to JM-1 cells, indicating that these cells possess receptors capable of binding only IL-3. Conversely, $^{125}$I-IL-3 does not bind to HL-60 cells nor does IL-3 inhibit binding of $^{125}$I-GM-CSF to HL-60 cells, indicating that these cells possess receptors capable of binding only GM-CSF. In contrast, both KG-1 and AML-193 cells bind $^{125}$I-GM-CSF and $^{125}$I-IL-3 and, in addition, both IL-3 and GM-CSF are able to partially compete specific binding of the heterologous radiolabeled ligand, with approximately equivalent capacities. This suggests that these cell lines possess receptors that bind only IL-3, receptors that bind only GM-CSF, and receptors that bind both GM-CSF and IL-3, all with high affinity.

In order to determine the affinity of binding ($K_I$) of IL-3, GM-CSF and GM-CSF/IL-3 fusion protein, inhibition assays were performed in which the ability of varying concentrations of these unlabeled proteins to inhibit binding of $^{125}$I-IL-3 to JM-1 cells, $^{125}$I-GM-CSF to HL-60 cells and $^{125}$I-IL-3 and $^{125}$I-GM-CSF to KG-1 and AML-193 cells were measured. Assays were performed by incubating cells ($3.3 \times 10^7$/ml) with $3 \times 10^{10}$M $^{125}$I-GM-CSF or $^{125}$I-IL-3 and varying concentrations of unlabeled IL-3, GM-CSF or GM-CSF/IL-3 fusion protein for 30–60 minutes at 37° C. Binding was assayed using the phthalate oil separation method disclosed by Dower et al. (*J. Immunol.* 132:751, 1984), essentially as described by Park et al. (*J. Biol. Chem.* 261:4177, 1986). Data was analyzed as described by Park et al. (*Blood* 74:56, 1989). Binding affinities were determined for IL-3, GM-CSF and GM-CSF/IL-3, as shown in Table B, below.

TABLE B

| Labeled Ligand | Unlabeled Competitor | $K_I$ Values (M$^{-1}$) | | | |
|---|---|---|---|---|---|
| | | JM-1 | HL60 | KG-1 | AML-193 |
| $^{125}$I-IL-3 | IL-3 | $1.8 \times 10^{10}$ | — | $2.0 \times 10^{10}$ | $4.1 \times 10^{9}$ |
| | GM-CSF/IL-3 | $6.1 \times 10^{9}$ | — | $2.8 \times 10^{11}$ | $1.5 \times 10^{10}$ |
| $^{125}$I-GM-CSF | GM-CSF | — | $1.2 \times 10^{10}$ | $3.2 \times 10^{10}$ | $1.6 \times 10^{10}$ |
| | GM-CSF/IL-3 | — | $6.8 \times 10^{9}$ | $1.9 \times 10^{10}$ | $1.5 \times 10^{10}$ |

The experiments used to obtain the data in Table B were conducted using different cell lines in different experiments and accordingly show some variation, making direct comparison difficult. In order to enable direct comparison of this data, the $K_I$ values of both the controls and the fusion proteins were normalized to the $K_I$ value for the control on one cell line. IL-3 data were normalized to a $K_I = 1.8 \times 10^{10}$M$^{-1}$ on JM-1 cells, and GM-CSF data were normalized to a $K_I = 1.2 \times 10^{10}$M$^{-1}$ on HL-60 cells to give the values as set forth below in Table C.

TABLE C

| Labeled Ligand | Unlabeled Competitor | Normalized $K_I$ Values (M$^{-1}$) | | | |
|---|---|---|---|---|---|
| | | JM-1 | HL60 | KG-1 | AML-193 |
| $^{125}$I-IL-3 | IL-3 | $1.8 \times 10^{10}$ | — | $1.8 \times 10^{10}$ | $1.8 \times 10^{10}$ |
| | GM-CSF/IL-3 | $6.1 \times 10^{9}$ | — | $2.5 \times 10^{11}$ | $6.8 \times 10^{10}$ |
| $^{125}$I-GM-CSF | GM-CSF | — | $1.2 \times 10^{10}$ | $1.2 \times 10^{10}$ | $1.2 \times 10^{10}$ |
| | GM-CSF/IL-3 | — | $6.8 \times 10^{9}$ | $7.1 \times 10^{9}$ | $1.1 \times 10^{10}$ |

Comparison of the normalized data indicates that the GM-CSF/IL-3 fusion protein and GM-CSF bind with approximately the same affinity to receptors for GM-CSF on HL-60, KG-1 and AML-193 cells. In contrast, the GM-CSF/IL-3 fusion protein and IL-3 bind with different affinities: GM-CSF/IL-3 fusion protein binds with lower affinity than IL-3 to receptors on JM-1 cells (which have only IL-3 binding receptors); in contrast, the GM-CSF/IL-3 fusion protein binds with a significantly higher affinity than IL-3 to receptors on KG-1 and AML-193 cells (both of which have GM-CSF/IL-3 receptors). Using the JM-1 cell line as a standard for normal binding affinity of the GM-CSF/IL-3 fusion protein to a receptor (i.e., for binding to a receptor which is capable of binding only a single ligand), the GM-CSF/IL-3 fusion protein binds to KG-1 cells with a 41.0-fold higher binding affinity, and to AML-193 cells with an 11.1-fold higher binding affinity.

Not wishing to be bound by any particular theory, it is believed that the higher binding affinity of GM-CSF/IL-3 fusion protein to KG-1 and AML-193 cells is related to the presence in both of these cell lines of the GM-CSF/IL-3 receptor. In particular, the higher binding affinity of the GM-CSF/IL-3 fusion protein to the AML-193 cell line may explain the higher biological activity of the GM-CSF/IL-3 fusion protein in the thymidine incorporation assay of Example 4 which utilized the AML-193 cell line.

EXAMPLE 6

Effect of GM-CSF/IL-3 on Proliferation of Human Bone Marrow

The biological effect of GM-CSF/IL-3 on the proliferation of unfractionated human bone marrow was compared with that of GM-CSF and IL-3 alone. Non-adherent, low density, T cell deplated cultures of human bone marrow were plated in methylcellulose (BFU-E, CFU-GEMM, 40,000 cells per plate) or agar (CFU-GM; 40,000 cells per culture) as described by Lu et al., *Blood* 61:250 (1983). Methylcellulose cultures contained 1 unit per plate erythropoietin and accounts for the background of $48 \pm 2$ BFU-E in the absence of cytokine. Cultures were incubated in a 5% $O_2$, 5% $CO_2$, 90% $N_2$ atmosphere for 14 days and counted with an inverted microscope. These values represent the mean $\pm 1$ standard deviation of duplicate or triplicate data points in one of two representative experiments.

TABLE D

| Cytokine | Dose (pg/ml) | Colonies (Mean ± S.D.) | | |
|---|---|---|---|---|
| | | CFU-GEMM | CFU-GM | BFU-E |
| None | | 0 | 3 ± 1 | 48 ± 2 |
| GM-CSF/IL-3 | 5000 | 10.3 ± 1 | 97 ± 2 | 107 ± 5 |
| | 2500 | 10.3 ± 0.9 | 74 ± 1 | 119 ± 5 |
| | 1250 | 6.8 ± 0.5 | 59 ± 2 | 125 ± 8 |
| | 625 | 4.3 ± 0.5 | 52 ± 6 | 83 ± 5 |
| | 312 | 2.5 ± 0.7 | 35 ± 2 | 70 ± 4 |
| | 156 | 1.0 ± 0.4 | 24 ± 3 | 49 ± 6 |
| | 78 | 0 | 16 ± 2 | 50 ± 3 |
| GM-CSF + IL-3 | 5000 + 5000 | 10.0 ± 0.7 | 54 ± 3 | 94 ± 6 |
| | 2500 + 2500 | 8.5 ± 0.5 | 52 ± 3 | 81 ± 3 |
| | 1250 + 1250 | 5.0 ± 0.4 | 47 ± 4 | 56 ± 3 |
| | 625 + 625 | 2.5 ± 0.3 | 27 ± 2 | 44 ± 3 |
| | 312 + 312 | 1.0 ± 0 | 14 ± 1 | 42 ± 3 |
| | 156 ± 156 | 0.3 ± 0.3 | 10 ± 1 | 44 ± 3 |
| GM-CSF | 5000 | 6.8 ± 0.6 | 42 ± 4 | 63 ± 3 |
| | 2500 | 3.5 ± 0.7 | 42 ± 2 | 61 ± 1 |
| | 1250 | 1.5 ± 0.3 | 33 ± 2 | 47 ± 4 |
| | 625 | 0.3 ± 0.3 | 21 ± 2 | 46 ± 3 |
| | 312 | 0 | 16 ± 1 | |
| IL-3 | 5000 | 4.0 ± 0.7 | 16 ± 0.3 | 67 ± 2 |
| | 2500 | 4.0 ± 0.4 | 9 ± 1 | 66 ± 2 |
| | 1250 | 1.3 ± 0.3 | 4 ± 1 | 49 ± 2 |
| | 625 | 0 | | 45 ± 3 |
| | 312 | 0 | | |

= value equal to media control
*$p < 0.05$ compared media control

TABLE E

| Cytokine | Dose (pg/ml) | Colonies (Mean + S.D.) | | |
|---|---|---|---|---|
| | | CFU-GEMM | CFU-GM | BFU-E |
| None | | 2 ± 0 | 0 | 44 ± 4 |
| GM-CSF/IL-3 | 5000 | — | 43 ± 5 | — |
| | 2500 | 10.0 ± 1* | 45 ± 5 | 125 ± 10* |
| | 1250 | 9.0 ± 0* | 23 ± 2 | 127 ± 7* |
| | 625 | 6.0 ± 1* | 15 ± 2 | 97 ± 2* |
| | 312 | 5.5 ± 0.5 | 8 ± 1 | 71 ± 1* |
| | 156 | 2.0 ± 1 | 5 ± 1 | 47 ± 3 |
| | 78 | 2.0 ± 0 | 2 ± 0.3 | 44 ± 1 |
| GM-CSF + IL-3 | 5000 + 5000 | 6.5 ± 1.5* | 32 ± 2 | 93 ± 3* |
| | 2500 + 2500 | 5.0 ± 1* | 21 ± 2 | 71 ± 8* |
| | 1250 + 1250 | 1.5 ± 0.5 | 13 ± 0.3 | 44 ± 2 |
| | 625 + 625 | 2.0 ± 0 | 7 ± 2 | 45 ± 5 |
| | 312 + 312 | | 3 ± 1 | |
| | 156 + 156 | | 1 ± 0.9 | |

= value equal to media control
*$p < 0.05$ compared to media control

Tables D and E indicate that GM-CSF plus IL-3 is approximately two fold more potent than either GM-CSF or IL-3 alone in enhancing proliferation of unfractionated human bone marrow cells. The GM-CSF/IL-3 fusion protein is equivalent in potentcy to a mixture of GM-CSF and IL-3, and that the mixture of GM-CSF and IL-3 showed an approximately two fold enhancement compared to GM-CSF or IL-3 alone.

EXAMPLE 7

Synthesis of cDNA Encoding IL-3/GM-CSF Fusion Protein

A cDNA encoding a fusion protein comprising an N-terminal IL-3 and a C-terminal GM-CSF was constructed as follows. The yeast expression vector pIXY120 (described in Example 1B) was digested with the restriction enzymes Asp718, which cleaves near the 3' end of the α-factor leader peptide (nucleotide 237), and Nco1, which cleaves in the polylinker. The large vector fragment was purified and ligated to an approximately 500 bp Asp718-Nco1 fragment (encoding GM-CSF(Leu$^{23}$Asp$^{27}$Glu$^{39}$)) from a partial digest of L207-3 (ATCC 67231), to yield pIXY273. A 9 kb Asp718-Bgl2 fragment of pIXY273 (still containing the GM-CSF(Leu$^{23}$Asp$^{27}$Glu$^{39}$) cDNA) was then ligated to an Asp718-Nru1 fragment encoding human IL-3 (Pro$^8$Asp$^{15}$Asp$^{70}$) from pIXY151 (described in Example 1B) and the following double stranded oligonucleotide:

This oligonucleotide overlaps the 3' end of IL-3 by 8 bp but does not include the stop codon, contains the Gly-Ser linker, and overlaps the 5' end of GM-CSF by 10 bp. The resulting vector was termed pIXY344 and was used to express an IL-3/GM-CSF fusion protein essentially as described above in Example 3.

EXAMPLE 8

Binding Activity of IL-3/GM-CSF Fusion Protein in Equilibrium Binding Assay

Binding affinities of human IL-3, GM-CSF and IL-3/GM-CSF fusion protein (produced as described in Example 8) for receptors on human cells lines were determined by inhibition of $^{125}$I-labeled IL-3 or GM-CSF binding as described in Example 5 above.

Binding assays were performed using JM-1, HL-60 and KG-1 cells, which were obtained and prepared as described by Park et al. (J. Biol. Chem. 264:5420, 1989). JM-1 cells possess receptors capable of binding IL-3, but not GM-CSF. Conversely, HL-60 cells possess receptors capable of binding GM-CSF, but not IL-3. KG-1 cells possess receptors for both GM-CSF and IL-3.

Binding affinities ($K_I$) were determined for IL-3, GM-CSF and GM-CSF/IL-3, as shown in Table F, below.

TABLE F

| Labeled Ligand | Unlabeled Competitor | $K_I$ Values (M$^{-1}$) JM-1 | HL60 | KG-1 |
|---|---|---|---|---|
| $^{125}$I-IL-3 | IL-3 | 6.0 × 10$^9$ | — | 5.7 × 10$^9$ |
|  | GM-CSF/IL-3 | 2.5 × 10$^9$ | — | 3.0 × 10$^{10}$ |
|  | IL-3/GM-CSF | 1.2 × 10$^9$ | — | 2.2 × 10$^{10}$ |
| $^{125}$I-GM-CSF | GM-CSF | — | 1.5 × 10$^{10}$ | N.D. |
|  | GM-CSF/IL-3 | — | 5.4 × 10$^9$ | N.D. |
|  | IL-3/GM-CSF | — | 3.0 × 10$^9$ | N.D. |

N.D. = no data available

The above data indicate that the GM-CSF/IL-3 and IL-3/GM-CSF fusion proteins bind to JM-1 cells with an affinity lower than that of IL-3 alone. In contrast, the GM-CSF/IL-3 and IL-3/GM-CSF fusion proteins bind to KG-1 cells with a significantly higher affinity than that of IL-3 alone. The $K_I$ value for both GM-CSF/IL-3 and IL-3/GM-CSF fusion proteins on KG-1 cells is 10–20 fold higher than on JM-1 cells. Similarly, the $K_I$ values determined for GM-CSF/IL-3 and IL-3/GM-CSF on HL-60 cells are similar.

In view of the data shown in Examples 4–6 (which show a correlation between binding affinity and enhanced biological activity), the above binding data suggest that the IL-3/GM-CSF fusion protein will have increased biological activity.

We claim:

1. A DNA sequence encoding a fusion protein comprising GM-CSF is fused to IL-3.

2. A DNA sequence encoding a fusion protein according to claim 7, wherein GM-CSF is fused to IL-3 via a linker peptide sequence.

3. A DNA sequence encoding a fusion protein according to claim 2, wherein the fusion protein is selected from the group consisting of the sequence of amino acids 1–271 depicted in FIG. 1 and the sequence of amino acids 1–275 depicted in FIG. 2.

4. A DNA sequence encoding a fusion protein comprising huGM-CSF/(Gly)$_4$ Ser(Gly)$_5$Ser/huIL-3.

5. A DNA sequence encoding a fusion protein wherein the human GM-CSF is selected from the group consisting of huGM-CSF, huGM-CSF(Leu$^{23}$Asp$^{27}$Glu$^{39}$), huGM-CSF(Leu$^{23}$), huGM-CSF(Leu$^{23}$Asp$^{27}$), huGM-CSF(Glu$^{39}$), huGM-CSF(Asp$^{27}$Glu$^{39}$), huGM-CSF(Leu$^{23}$Glu$^{39}$) and huGM-CSF(Asp$^{27}$) and human IL-3 is selected from the group consisting of huIL-3, huIL-3(Pro$^8$Asp$^{15}$Asp$^{70}$), huIL-3(Asp$^{15}$Asp$^{70}$), huIL-3(Pro$^8$Asp$^{15}$), huIL-3(Pro$^8$Asp$^{70}$), and huIL-3(Asp$^{70}$) huiL-3(Asp$^{15}$).

6. A recombinant expression vector comprising a DNA sequence according to claim 1.

7. A recombinant expression vector comprising a DNA sequence according to claim 2.

8. A recombinant expression vector comprising a DNA sequence according to claim 3.

9. A recombinant expression vector comprising a DNA sequence according to claim 4.

10. A recombinant expression vector comprising a DNA sequence according to claim 5.

11. A process for preparing a fusion protein comprising GM-CSF and IL-3, comprising the step of culturing a suitable host cell comprising a vector according to claim 6 under conditions promoting expression.

12. A process for preparing a fusion protein comprising GM-CSF and IL-3, comprising the step of culturing a suitable host cell comprising a vector according to claim 7 under conditions promoting expression.

13. A process for preparing a fusion protein comprising GM-CSF and IL-3, comprising the step of culturing a suitable host cell comprising a vector according to claim 8 under conditions promoting expression.

14. A process for preparing a fusion protein comprising GM-CSF and IL-3, comprising the step of culturing a suitable host cell comprising a vector according to claim 9 under conditions promoting expression.

15. A process for preparing a fusion protein comprising GM-CSF and IL-3, comprising the step of culturing a suitable host cell comprising a vector according to claim 10 under conditions promoting expression.

* * * * *

UNITED STATES PATENT AND TRADEMARK OFFICE
CERTIFICATE OF CORRECTION

PATENT NO. : 5,108,910
DATED : April 28, 1992
INVENTOR(S) : Benson M. Curtis et al.

It is certified that error appears in the above-identified patent and that said Letters Patent is hereby corrected as shown below:

Column 19, line 34, change filler to -- filter --.

IN THE CLAIMS:

In Claim 1, delete "is".

In Claim 2, delete "7" and replace with -- 1 --.

In Claim 4, delete "huGm-CSF/(Gly)$_4$Ser(Gly)$_5$Ser/huIL-3" and replace with -- huGM-CSF[Leu$^{23}$Asp$^{27}$Glu$^{39}$]/(Gly)$_4$Ser(Gly)$_5$Ser/huIL-3[Pro$^8$Asp$^{15}$Asp$^{70}$] --.

In Claim 5, delete "huIL-3(Asp$^{70}$)" from line 9 and add -- huIL-3(Asp$^{70}$) --, after "huIL-3(Pro$^8$Asp$^{15}$Asp$^{70}$)".

In Claim 5, last line, delete "huiL-3(Asp$^{15}$)" and replace with huIL-3(Asp$^{15}$)--.

Signed and Sealed this

Twenty-ninth Day of June, 1993

Attest:

MICHAEL K. KIRK

*Attesting Officer*      *Acting Commissioner of Patents and Trademarks*